United States Patent [19]

Gordon et al.

[11] Patent Number: 4,498,796
[45] Date of Patent: Feb. 12, 1985

[54] SURGICAL SCRUB

[75] Inventors: Marvin Gordon, East Windsor; Joseph Lichtenstein, Colonia, both of N.J.

[73] Assignee: Whitman Medical Corporation, Clark, N.J.

[21] Appl. No.: 476,348

[22] Filed: Mar. 17, 1983

Related U.S. Application Data

[63] Continuation-in-part of Ser. No. 435,335, Oct. 19, 1982, , which is a continuation-in-part of Ser. No. 298,246, Aug. 31, 1981, Pat. No. 4,415,288, and a continuation-in-part of Ser. No. 241,486, Mar. 9, 1981, abandoned.

[51] Int. Cl.³ .................... A47L 13/17; A61M 35/00
[52] U.S. Cl. .................................. 401/132; 401/134; 401/196; 401/207; 604/3
[58] Field of Search ............... 401/133, 132, 196, 134, 401/207; 604/3

[56] References Cited

U.S. PATENT DOCUMENTS

| 2,229,749 | 1/1941 | Little | 401/135 |
| 2,979,030 | 4/1961 | Harrington | 401/196 X |
| 3,061,868 | 11/1962 | Miller | 401/135 |
| 3,481,676 | 12/1969 | Schwartzman | 401/134 |
| 3,774,609 | 11/1973 | Schwartzman | 401/134 X |
| 4,415,288 | 11/1983 | Gordon et al. | 401/132 |

FOREIGN PATENT DOCUMENTS 69744 11/1958 France ............................. 401/207

Primary Examiner—Steven A. Bratlie
Attorney, Agent, or Firm—Holman & Stern

[57] ABSTRACT

A surgical scrub apparatus includes a liquid-containing rupturable cylindrical cartridge which is slidable within a tubular handle having at least one and preferably two hollow interior spikes projecting longitudinally from one end. The cartridge can be inserted sufficiently far to cause rupture of the cartridge by both spikes. Liquid from the ruptured cartridge flows from within the handle, preferably through the spikes, to an applicator sponge having two wide area applicator surfaces. The spikes include exterior projections which are received in respective recesses or flow passages in the applicator to facilitate distribution of liquid through the applicator to the application surfaces. The recesses are contoured as desired to aid in liquid distribution. The interior of the spikes may be coated with a non-wetting agent such as silicone to facilitate flow through the hollow spikes.

28 Claims, 14 Drawing Figures

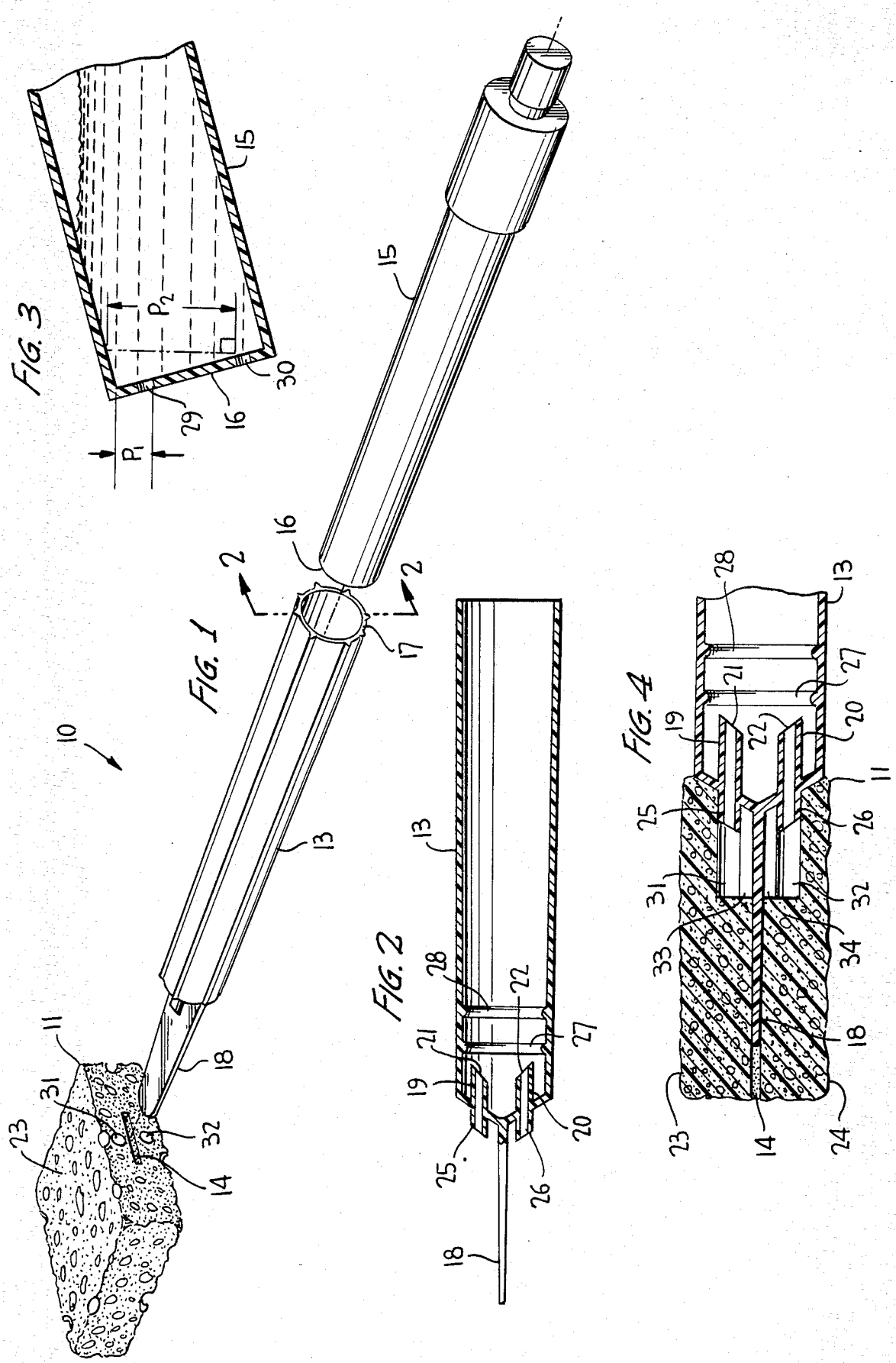

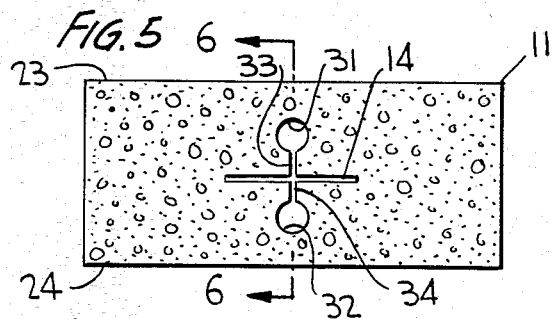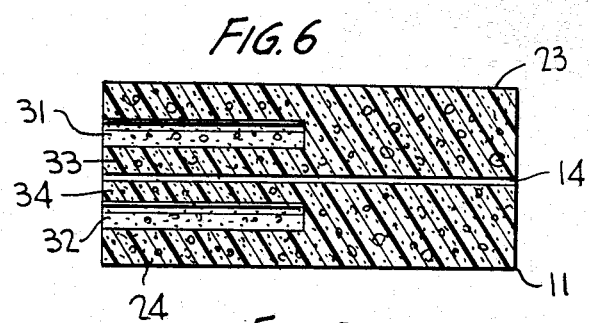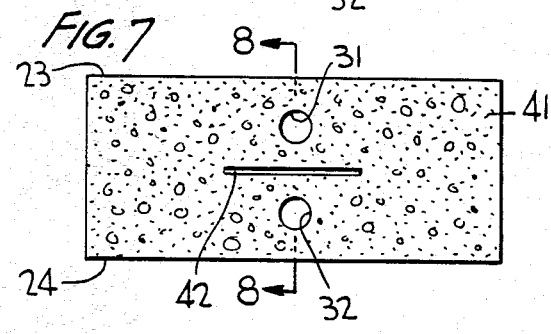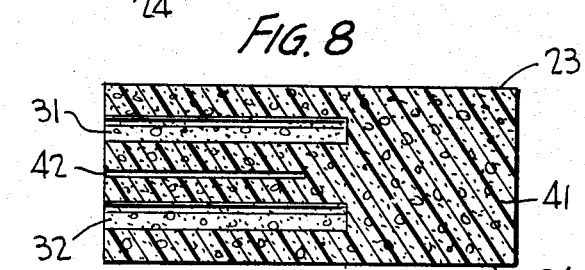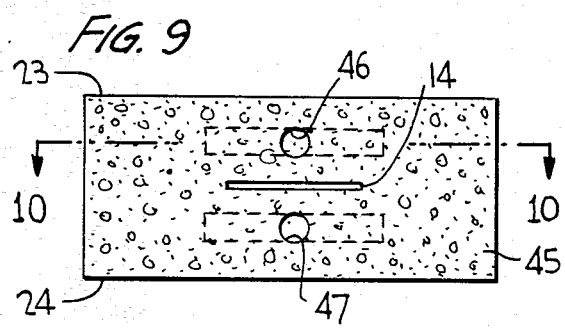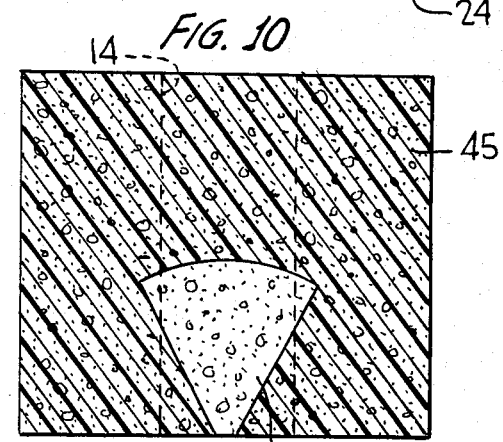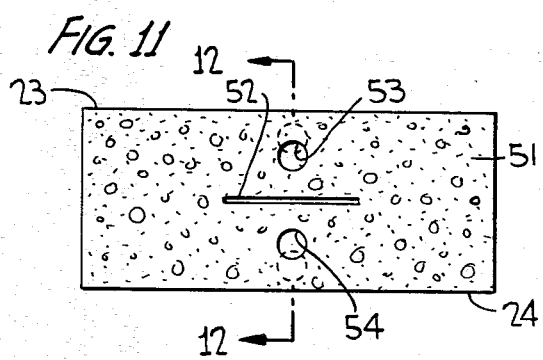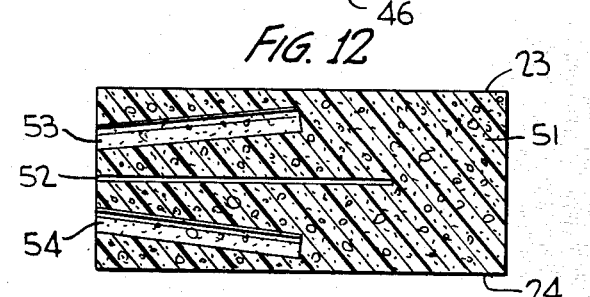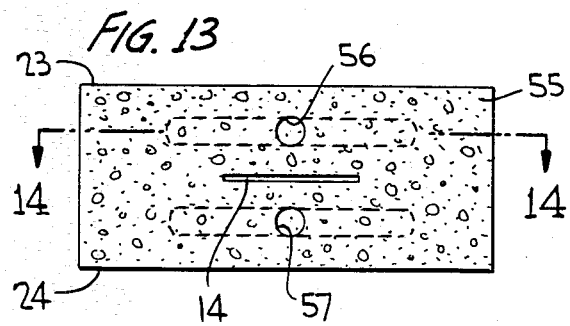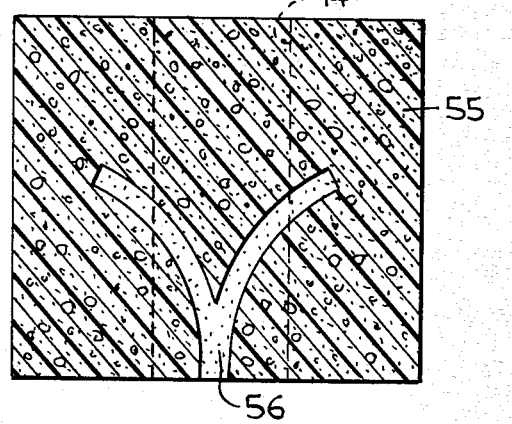

SURGICAL SCRUB

CROSS-REFERENCE TO RELATED APPLICATIONS

This application is a continuation-in-part application of our pending U.S. patent application Ser. No. 435,335, filed Oct. 19, 1982 and entitled "Surgical Scrub", which is a continuation-in-part application of our U.S. patent application Ser. No. 241,486, filed Mar. 9, 1981 now abandoned and entitled "Improved Liquid Dispensing Device", and a continuation-in-part application of U.S. patent application Ser. No. 298,246, filed Aug. 31, 1981 and entitled "Improved Liquid Dispensing Device" now U.S. Pat. No. 4,415,228.

BACKGROUND OF THE INVENTION

1. Technical Field

The present invention relates generally to liquid dispensers and applicators of the type wherein a premeasured supply of liquid is disposed in an applicator handle and selectively dispensed through the applicator. The invention has particular applicability in the field of aseptic surgery preparation, as a pre-operative surgical scrub system for use in the operating room.

2. The Prior Art

As part of the preparation for many surgical procedures, for example, a surgical operation, it is required that the affected area of the patient be antiseptically cleansed. This requirement has existed for a very long time and the procedures used to meet this requirement have changed over the years. Originally, jars or cans of gauze, sponges or cotton balls were packed, sterilized and placed in operating rooms. These sponges and/or cotton balls are used for scrubbing procedures by holding them with sterile forceps and dipping them into a can containing a soap or antiseptic solution. After the cotton ball or sponge is saturated with solution, it is wiped onto the appropriate area. This procedure is inconvenient for a number of reasons. First, it tends to create a mess due to the open pan and the constant back and forth travel of the sponge or cotton ball between the pan and the patient. Further, the procedure takes an undesirably long time and results in an inordinate amount of liquid being lost due to splashing, scattering and waste. Moreover, this procedure tends to use more antiseptic solution than necessary because most medical personnel mistakenly believe that the antiseptic effect is more readily obtained if more solution is used. This is not true and, quite to the contrary, it has been noted that excess solution tends to form pools or puddles under the patient, resulting in iodine burns.

Apart from the disadvantage of the forceps and sponge or cotton ball procedures, the lack of standardization of techniques resulted in considerable confusion. Eventually, certain standards did develop. Specifically, the area of the incision on the patient's body must be cleansed thoroughly with a scrub or soap solution for a period of between 3–10 minutes. Most surgical operations, other than orthopedic surgery, require 3 minutes of scrubbing time; orthopedic surgery required 10 minutes of scrubbing time due to the increased risk of infection. After the scrubbing procedure, the area is dried with a sterile wipe and antiseptic solution is applied. For some procedures, other than orthopedic surgery, the scrub portion of the procedure is eliminated and only the antiseptic solution is applied. In either case, the standard procedure for applying either the scrub or antiseptic solution involves starting from the middle of the treated area and proceeding outward in circular or square motions, it being important never to return to a previously treated area with the same surface of the sponge. The sponge may be turned over and the same procedure started once again; that is, as long as a new sponge surface area is used, an already-prepared skin area may be re-contacted. However, one should never apply a used or contaminated sponge surface to a previously prepared skin area.

Attempts to overcome the drawbacks described above in relation to surgical swab and/or scrub apparatus and techniques involved the development of devices in which the liquid to be applied is contained within the device itself, generally in a hollow handle. Examples of such devices may be found in the following U.S. Pat. Nos. 1,221,227; 2,333,070; 3,324,855; 3,508,547; 3,614,245; 3,774,609; 3,847,151; 3,876,314; 3,891,331; 3,896,808; 3,958,571; 4,148,318; and 4,225,254. The devices disclosed in these patents present considerable improvements over the relatively primitive method of employing individual cotton balls or sponges with forceps and dipping these into the pan of solution as described above. However, many of the devices disclosed in the aforesaid patents are relatively complex to manufacture, thereby resulting in too high a cost for a device which is disposable after a single use. Moreover, many of the devices disclosed in these prior patents have only one available surface for the applicator sponge or swab. For example, the device disclosed in U.S. Pat. No. 4,225,254 provides a generally conical-shaped sponge, thereby making it difficult to assure that the same surface area of the sponge does not contact an already treated area of the patient's skin. Moreover, the conical configuration minimizes the available surface area of the sponge. As noted above, available clean and unused surface area of the preparation sponge is one of the most important factors governing the pre-surgical preparation technique.

The device disclosed in U.S. Pat. No. 3,847,151 had considerable promise toward solving most of the problems referred to above. That patent discloses a surgical scrub device wherein a sponge applicator is mounted on a nozzle which extends from a hollow handle containing antiseptic solution. The nozzle includes a joint which can be selectively ruptured prior to use so as to permit the solution to flow from the nozzle into the sponge. In practice, however, this device proved to have functional problems. Mass production techniques being what they are, the stress break at the rupturable joint in the nozzle is not always complete and fluid is not always available. In addition, the rupture is not always properly completed by the user of the device, again resulting in a situation where fluid is not available for use. An additional problem with this device is that scrub solution (soap) tends to fill the sponge too slowly, whereas swab solution (antiseptic) tends to fill the sponge too quickly. In general, the product, although well conceived, has proven not to be reliable in use.

It has been suggested (see U.S. Pat. No. 3,481,676 to Schwartzman) that a liquid applicator may take the form of a cylindrical rupturable liquid-filled cartridge disposed in a tube-like handle having a sharp-edged flow passage disposed therein. The cartridge can be forced against the sharp edge to rupture the cartridge and extend the flow passage through the rupture. This permits liquid to flow from the cartridge, through the passage, to an applicator which surrounds the passage. The approach disclosed by Schwartman is valid for many applicators wherein a slow rate of fluid application can be tolerated. More particularly, in order for the liquid to be able to flow from the ruptured cartridge, there must be air admitted into the cartridge to replace the outflowing liquid. In the Schwartzman device, inflowing air and outflowing liquid must flow in opposite directions through the single sharp-edged flow passage. This severly limits the liquid outflow rate. For surgical scrub applications, it is important that the sponge or applicator be quickly saturated so that the liquid can be quickly applied to the pre-surgical incision site without delaying the surgical procedure. This problem could be remedied in the Schwartzman applicator by providing the cartridge with a valved or other permanent vent opening, much like is done with the cartridge-type fountain pens. However, such opening would not be a satisfactory solution for surgical scrub applications where the administered liquid must be maintained sterile in the cartridge.

In our aforesaid U.S. patent application Ser. No. 435,335, the subject matter of which is expressly incorporated herein by reference, we disclosed an improved surgical swab or scrub device wherein an elongated tubular handle has an applicator sponge permanently or removably secured to one end thereof and accepts the cylindrical cartridge of liquid at its other end. The sponge, which receives a flexible paddle-like member, has two opposite applicator sides. Two rigid hollow spikes are transversely spaced on opposite sides of the paddle-like member but inside the one handle end so as to point toward the other handle end. The spikes are in position to rupture a forward end of the cartridge when the cartridge is fully inserted into the handle, and to conduct liquid from the cartridge out to the sponge or applicator. The spikes are also positioned such that one or the other is always vertically higher than the other when the sponge is deployed for use with its applicator surfaces substantially horizontal. This difference in height reflects itself as a difference in liquid pressure at the punctures in the cartridge, whereby vent air can freely enter the cartridge through the lower pressurized upper puncture, thereby permitting liquid to freely egress through the lower puncture. The spikes are formed on respective diagonals which reside in respective bias planes which converge toward the said one end of the handle. This maximizes the spacing between two given puncture locations and thereby increases the liquid pressure difference at the puncture.

We have found that, for some liquids, even this increase pressure difference is not sufficient to satisfactorily distribute the liquid at a sufficient rate over a wide enough area of the applicator surfaces.

OBJECTS AND SUMMARY OF THE INVENTION

It is therefore an object of the present invention to provide a simple, inexpensive and disposable surgical scrub device which is capable of administering sterile liquid to an incision site for swabbing or scrubbing that site in pre-surgical procedures. It is a further object of the present invention to provide such a device which is devoid of the disadvantages enumerated above in the devices of the afore-mentioned patents. It is another object of the present invention to provide such a device useful as a swab or scrub, depending upon the selection of a replacement cartridge of the liquid to be applied. It is still another object of the present invention to provide a surgical swab or scrub device of the type wherein liquid to be applied is contained within the handle and wherein the liquid can be reliably and quickly applied to the applicator. It is another more specific object of the present invention to provide an improved version of the surgical scrub unit described in our aforesaid U.S. patent application Ser. No. 435,335 whereby liquid flows freely and is optimally distributed along the applicator surfaces of the unit.

We have found that the aforesaid deficiencies in our prior surgical scrub unit for certain liquids results from the impedance to flow presented by the sponge material itself. Specifically, in our prior unit, the exterior ends of the hollow spikes terminate flush with the handle and are abutted by the applicator or sponge material. The egressing liquid is quickly absorbed by the saturated applicator material and flows at a reduced rate only to the nearest portion of the applicator surfaces.

In order to solve this problem, the hollow spike flow passages are projected a short distance beyond the end of the handle along opposite sides of the paddle-like member. In addition, the applicator is provided with corresponding flow channels which receive and extend beyond the projected flow passages. Outflow from the projected flow passages is thereby not directed immediately into impeding saturated applicator material, but instead flows through the extended channels. The channels may be extended in different contours, as desired, to optimize distribution of the flowing liquid along the applicator surfaces. In certain cases, the flow of liquid from the cartridge to the sponge applicator surfaces is improved even more by placing a thin coating of a silicone or other non-wetting agent along the interior wall of each hollow spike and its external projection.

BRIEF DESCRIPTION OF THE DRAWINGS

The invention will now be more fully understood, while still further objects and advantages will become apparent, in the following detailed description of embodiments thereof illustrated in the accompanying drawings wherein like components in the various figures are designated by the same reference numerals:

FIG. 1 is an exploded view in perspective of a preferred embodiment of the improved surgical scrub device of the present invention;

FIG. 2 is a view in section taken along lines 2—2 of FIG. 1;

FIG. 3 is a diagrammatic illustration of the cartridge shown in FIG. 1, illustrating the pressure conditions established by rupture of the cartridge;

FIG. 4 is an enlarged detailed view in section of one end of the handle member and applicator of FIG. 1, showing the manner in which flow from the handle is freely distributed into the applicator;

FIG. 5 is a front view in elevation of the applicator of FIG. 4;

FIG. 6 is a view in section taken along lines 6—6 of FIG. 5;

FIG. 7 is a front end view in elevation of a modified applicator of the present invention;

FIG. 8 is a view in section taken along lines 8—8 of FIG. 7;

FIG. 9 is a front end view in elevation of another modified applicator of the present invention;

FIG. 10 is a view in section taken along lines 10—10 of FIG. 9;

FIG. 11 is a front end view in elevation of a modified applicator of the present invention;

FIG. 12 is a view in section taken along lines 12—12 of FIG. 11;

FIG. 13 is a front view in elevation of a further modified applicator of the present invention; and FIG. 14 is a view in section taken along lines 14—14 of FIG. 13.

DESCRIPTION OF THE PREFERRED EMBODIMENTS

A surgical scrub device 10, constituting the preferred embodiment of the present invention, is illustrated in FIGS. 1-6 to which specific reference is now made. Surgical scrub device 10 is made of three separate parts, namely, an applicator 11, a tubular handle 13 and a liquid containing cartridge 15. Applicator 11 is the same type of applicator which is described in our afore-mentioned U.S. patent application Ser. No. 435,335 and partakes of all the desired features and considerations set forth for those applicators. It should be noted that, although applicator 11 is preferably a sponge, it can be made of other materials which absorb liquid and distribute the absorbed liquid when compressed. Likewise, cartridge 15 is functionally and structurally similar to the cartridges described in the aforesaid patent application and partakes of the same design features and considerations for the cartridges set forth therein.

Handle member 13 is a rigid, plastic, hollow tube having an open rearward end 17 adapted to receive cartridge 15 therein when the forward end 16 of the cartridge is inserted first into the handle. The opposite or forward end of handle member 13 has a paddle-shaped projection 18 which is adapted to be received in a suitably provided slot 14 in an applicator 11. In this manner, paddle 18 serves to support the applicator 11 and permits compression of one of the applicator surfaces 23, 24 against a presurgical incision site by tilting the paddle end of the handle downward against that site. For this purpose, the paddle 18 is made somewhat flexible transversely of the longitudinal dimension of the handle in order to permit flexure and compression of the applicator relative to the handle.

The interior surface of the forward end of handle 13 is generally concave and has a pair of radially or transversely spaced hollow spikes 19, 20 projecting therefrom toward the open rearward end 17 of the handle. Spikes 19 and 20 are respective tubular projections which are terminated along respective bias planes 21, 22 which converge toward one another in a direction toward the paddle 18. This orientation of the spike-forming bias planes provides the greatest possible transverse spacing between the pointed ends of the spikes. This spacing feature, as described in detail below, increases the free flow of liquid from the punctured cartridge 15. The hollow interiors of spikes 19, 20 are preferably coated with a lining of silicone or other non-wetting film to facilitate flow through the spikes. The spikes extend as respective projections 25, 26 beyond the forward end of handle 13. Spikes 19 and 20, and their respective projections 25 and 26, are disposed on opposite transverse sides of paddle 18. Preferably, the longitudinal center lines of the hollow spikes 19 and 20 and respective projections 25 and 26 reside in a plane which perpendicularly bisects paddle 18 so that the spikes and projections are centered relative to the transverse dimension of the paddle. The goal, in any event, is to maximize the spacing between the cartridge punctures made by spikes 19, 20 to assure that one spike is always higher than the other when the applicator surfaces of the applicator 11 are oriented substantially horizontally, and to project the spike flow passages beyond the forward end of the handle.

A narrow annular shoulder 27 projects radially inward from the interior wall of tube handle 13 at an axial location just rearward of the rearward extremities of spikes 19, 20. A similar annular shoulder 28 projects radially inward from the interior wall of handle 13 at a location spaced slightly rearward of shoulder 27. Shoulder 28 serves as a stop for the forward end 16 of the cartridge 15 when the cartridge is inserted into the handle 13. To this end, the axial position of shoulder 28 is such that, when it stops further insertion of the cartridge into the handle 13, the forward end 16 of the cartridge is spaced from the rearward extremity of spikes 19, 20. In a manner similar to that described in our afore-mentioned U.S. patent application Ser. No. 435,335 cartridge 15 can be forced beyond the stop shoulder 28 so that the forward end 16 of the cartridge can be punctured by the spikes. Shoulder 27 serves as a fluid seal, in conjunction with the peripheral wall of ruptured cartridge 15, to prevent fluid from the ruptured cartridge from flowing rearwardly in the handle member 13. Handle member 13 may be provided with longitudinally-extending cut-out slots, if desired, to facilitate radial compression of the handle member and thereby force liquid from the cartridge into the applicator 11.

Free outflow from the cartridge can best be explained with the aid of the diagrammatic illustration of cartridge 15 presented in FIG. 3. The forward end 16 of the cartridge is illustrated with two punctures 29 and 30 which are assumed to have been made by respective spikes 19 and 20. These spikes have been omitted from the illustration in FIG. 3 for purposes of preserving diagrammatic clarity. Cartridge 15 is illustrated with its forward end tipped slightly downward from horizontal, as would be the case when the unit is in use. Since the applicator surfaces are substantially horizontal in use, paddle 18 is tilted slightly downward from horizontal and flexed back toward horizontal against the pre-surgical site. Therefore, puncture 29 will be disposed at a higher level than puncture 30. It should be noted that, if the handle is rotated 180° about its central longitudinal axis, so that the applicator surfaces are reversed in position, puncture 30 will be disposed at a higher level than puncture 29 and the same advantageous free-flow operation ensues. In either case, the liquid pressure head at the higher level puncture (29 in the present example) is relatively small and is designated $P_1$ in FIG. 3. This pressure is determined by the vertical height of liquid subsisting in the cartridge above puncture 29. The pressure head at the lower puncture 30 is designated $P_2$ and is determined by the vertical height of liquid subsisting above puncture 30 in the cartridge. Since puncture 30 is considerably lower in the cartridge than puncture 29, the pressure $P_2$ is considerably greater than the pressure of $P_1$. If $P_1$ is sufficiently low relative to atmospheric pressure, air enters puncture 29 via projection 25 and hollow spike 29, and liquid flows out through puncture 30, spike 20 and projection 26 to applicator 11. As the handle and cartridge are tilted more and more toward vertical (counter-clockwise in FIG. 3), the vertical column of liquid above upper puncture 29 increases in height, thereby increasing liquid pressure $P_1$ at puncture 29. At some position of the cartridge the liquid pressure $P_1$ is sufficiently greater than atmospheric pressure so that air does not readily enter the cartridge via puncture 19. However, the normal orientation of the surgical scrub device, in use, is with its forward end tilted just slightly downward from horizontal, in which position the pressure $P_1$ is close to a minimum and, in any event, is less than atmospheric pressure.

It will be appreciated that the greater the spacing between punctures 29 and 30, the greater will be the pressure differential caused by the liquid in the cartridge. Further, it is important that the punctures 29 and 30 be as close to the circumferential periphery of forward edge 16 of the cartridge as possible so that the pressure $P_1$ can be made as low as possible relative to ambient pressure. More specifically, when the punctures are very close to the rim of the forward edge 16 of the cartridge 15, the height of liquid in the cartridge above the puncture, which height produces the pressure $P_1$, is minimized for any orientation of the cartridge.

Free flow and distribution of liquid into applicator 11 is achieved by means of recesses 31 and 32 defined in the applicator. More specifically, recesses 31 and 32 are extended into the applicator from the front surface thereof on opposite sides of slit 14. These recesses are positioned to receive respective projections 25 and 26 of the handle and serve as flow passages for conducting liquid from projections 25 and 26 into the applicator interior. It is noted that, in the preferred embodiment, recesses 31 and 32 are parallel to one other and extend to a greater length within the applicator than the length of projections 25 and 26. The parallel relation is not crucial, as will be seen from the embodiments described hereinbelow. However, it is important that the length of recesses 31 and 32 be greater than the length of projections 25 and 26 so that flow from the projections can enter a portion of the applicator which is not impeded by saturated applicator material. From recesses 31 and 32 the liquid is readily distributed through the applicator to relatively large areas of applicator surfaces 23 and 24.

In the embodiment of FIG. 1–6, slit 14, which is wide enough and of sufficient height to just receive and engage paddle member 18, extends in length throughout the entire length of applicator 11. In addition, slits 33 and 34 are defined in applicator 11 perpendicular to slit 14 and extending from slit 14 to respective recesses 31 and 32. These features facilitate formation of the applicator in accordance with the present invention, particularly when the applicator is a sponge. For example, the slits in the sponge are readily formed as part of a die cut. Recesses 31, 32 are more easily burned or otherwise bored into the sponge applicator. Variations from this specific configuration are illustrated in FIGS. 7–14 to which specific reference is now made.

In the applicator embodiment of FIGS. 7 and 8, applicator 41 has a paddle-receiving slit 42 and recesses 31, 32 defined therein without interconnecting slits 33, 34 of FIGS. 5 and 6. In addition, slit 42 extends only a relatively short distance lengthwise into the applicator, rather than throughout the applicator length. In a functional sense, it is only necessary that slit 42 be long enough to receive the entire paddle member 18 so that the paddle member is properly engaged at the forward end of the handle.

In the applicator embodiment of FIGS. 9 and 10, applicator 45 has a paddle-receiving slit 14 which extends entirely through the length of the applicator. The flow projection receiving recesses 46, 47, instead of extending as tubular bores, are generally fan-shaped and diverge interiorally of the applicator from the applicator forward end. The widened internal areas of recesses 46, 47 are quite effective to distribute liquid received from projections 25, 26 to large areas of the applicator surfaces 23, 24. Recesses 46, 47 are shown as being defined in parallel planes; however, the planes of these divergent recesses may be skewed planes, if desired.

Applicator 51 illustrated in FIGS. 11 and 12 includes a paddle-receiving slit 52 which extends less than all the way through the applicator length, but which is longer than recesses 53 and 54. The recesses in this embodiment are generally tubular and diverge from one another and from slit 52. Thus, the interior terminations of recesses 53 and 54 are closer to respective applicator surfaces 23 and 24 than are the projection-receiving inlet ends of these recesses. For certain applications it may be desirable to provide converging rather than diverging recesses and this is certainly within the scope of the present invention.

In applicator 55 illustrated in FIGS. 13 and 14, the paddle-receiving slit 14 extends lengthwise through the entire applicator. The fluid-receiving recesses 56 and 57 are each bifurcated internally of the applicator to form two divergent flow passages. Of course, the concept of internally dividing the recesses is not limited to providing only two flow passages or to disposing the divided passages in a common plane as illustrated in FIGS. 13 and 14. Rather, within the scope of the present invention, there can be any number of divided passages, any of which may converge or diverge with respect to the paddle-receiving slit of 14.

In a typical but by no means limiting configuration of the preferred embodiment of FIGS. 1–6, the various parts have the following dimensions. Cartridge 15 is six inches long and has a 0.652 inch diameter. Applicator 11 is a sponge which is ⅞ inch deep and has top and bottom surfaces which are 1¾ inches square. The overall length of handle member 13 is 5.512 inches, the paddle-shaped projection 18 being one inch long. The inner diameter of handle 13 is 0.687 inch and the thickness of the walls of handle 13 is approximately 0.069 inch. Each spike 19, 20 has an inner diameter of 0.114 inch and an outer diameter of 0.184 inch. The spike-forming bias cut is made at a 30° angle from the longitudinal axis of the handle so that the bias planes 21, 22 converge at a 60° angle. The projections 25, 26 extend ⅛ inch from the end of handle 13. Paddle 18 is preferably as thin as possible to enhance flexibility and its distal end is preferably rounded rather than squared off. Recesses 31, 32 extend approximately halfway into applicator 11. The unit as described is simple and inexpensive to fabricate and is therefore readily disposable after a single use. Specifically, the unit, in the optimal case, may be fabricated from only three separate components, namely, the applicator, the cartridge and the tubular handle. The cartridges, of course, may be interchangeable so that a variety of different liquids may be employed during the same procedure. The cartridges are easily changed and their contents remain sterile until used. The user of the device need not wear a surgical glove in view of the sterility of the cartridge arrangement as illustrated. The unit may be simply activated by merely grasping the handle in one hand and gently rapping the end of the cartridge on a hard surface so as to force the forward end of the cartridge against the spikes. Actuation is thus reliable and easily effected and the liquid to be dispensed flows freely to the applicator.

While we have described and illustrated specific embodiments of our invention, it will be clear that variations of the details of construction which are specifically illustrated and described may be resorted to without departing from the true spirit and scope of the invention as defined in the appended claims.

What is claimed is:

1. A surgical scrub device comprising:
   an absorbent compressible applicator member;
   an elongated hollow handle member having first and second longitudinally-spaced ends, said first end being open, said second end being at least partially disposed in said absorbent applicator member, said handle member being adapted to receive an elongated fluid-containing cartridge in longitudinally slidably relation within said handle member, said cartridge having a rupturable forward end by which it is insertable into said open first end of said handle member; and
   first and second transversely spaced hollow spikes disposed inside said handle member proximate said second end, each spike having a pointed end projecting longitudinally toward said first end, each hollow spike providing flow communication from within said handle member to within said applicator member through said second end of said handle member;
   wherein said spikes are positioned to provide two transversely-spaced punctures in said forward end of said cartridge in response to a predetermined slidable insertion of said cartridge in said handle member;
   wherein said spikes include respective projecting portions which project in spaced relation externally of said hollow handle member beyond said second end; and
   wherein said applicator member has first and second flow passages in the form of respective first and second bores defined therein oriented to receive respective projecting portions of said spikes, each flow passage extending beyond its received projecting spike portions.

2. The surgical scrub device according to claim 1 further comprising a transversely flexible paddle extending from said second end of said handle member between and beyond said projecting portions of said spikes, wherein said applicator member has a slit defined therein between said flow passages to receive said flexible paddle and thereby engage said handle member.

3. The surgical scrub device according to claim 2 wherein said applicator member is a sponge-like member and has first and second opposite applicator surfaces, wherein said paddle has first and second opposite flat surfaces, and wherein said first and second hollow spikes and said flow passages provide flow communication from the interior of said handle member to locations along said first and second flat surfaces, respectively, of said paddle.

4. The surgical scrub device according to claim 3 wherein said first and second spikes are hollow tubes terminating along respective first and second bias planes to define said pointed ends, wherein said first and second bias planes converge in a direction toward said second end of said handle member.

5. The surgical scrub device according to claim 3 further comprising additional slits defined in said sponge-like member and extending perpendicular to said first-mentioned slit between said first-mentioned slit and said first and second flow passages, respectively.

6. The surgical scrub device according to claim 3 wherein said first and second flow passages in said sponge-like member are generally tubular passages extending generally parallel to said slit.

7. The surgical scrub device according to claim 6 wherein said first and second flow passages are each longer than said slit.

8. The surgical scrub device according to claim 6 wherein said first and second flow passages are each shorter than said slit.

9. The surgical scrub device according to claim 3 wherein said first and second flow passages each gradually widen along their lengths within said applicator member.

10. The surgical scrub device according to claim 3 wherein said first and second flow passages define an acute angle in a plane which is perpendicular to said slit.

11. The surgical scrub device according to claim 10 wherein said acute angle is a divergence between said first and second flow passages in a direction away from the received projecting portions.

12. The surgical scrub device according to claim 3 wherein said first and second flow passages each branch into plural further flow passages.

13. The surgical scrub device according to claim 1 wherein the hollow spikes are interiorally coated with a non-wetting material.

14. A surgical scrub device comprising:
    an absorbent compressible applicator member;
    an elongated hollow handle member having first and second longitudinally-spaced ends, said first end being open, said second end having a thin flexible member extending longitudinally therefrom to be received within said applicator member;
    an elongated fluid-containing cartridge adapted for longitudinal slidability in said handle member, said cartridge having a rupturable forward end by which it is insertable into said open first end of said handle member;
    at least one spike disposed inside said handle member proximate said second end, said spike having a pointed end projecting longitudinally toward said first end to puncture said forward end of said cartridge in response to a predetermined slidable insertion of said cartridge into said handle member; and
    flow passage means communicating with the interior of said handle member at said second end and projecting exteriorally of said handle member beyond said second end in a projecting portion;
    wherein said applicator member has at least one recess defined therein oriented to receive the projecting portion of said flow passage means, said recess comprising a bore extending deeper into said applicator member than said projecting portion to preclude impedance to flow into the applicator member by saturation of applicator member material at said projecting portion.

15. The surgical scrub device according to claim 14 wherein said applicator member has a slit defined therein to receive the flexible member, thereby to engage said handle member.

16. The surgical scrub device according to claim 15 wherein said applicator member has an exterior application surface, wherein said flow passage means and said recess provides flow communication from the interior of said handle member to the interior of said applicator member to facilitate flow to locations along said application surface.

17. The surgical scrub device according to claim 16 wherein said spike is a hollow tube, the interior of which comprises said flow passage means.

18. The surgical scrub device according to claim 15 further comprising an additional slit defined in said applicator member extending perpendicular to said first-mentioned slit between said first-mentioned slit and said recess.

19. The surgical scrub device according to claim 14 wherein said recess in said applicator member is a generally tubular passage.

20. The surgical scrub device according to claim 14 wherein said recess gradually widens along its length.

21. The surgical scrub device according to claim 14 wherein said recess defines an acute angle with said thin flexible member.

22. The surgical scrub device according to claim 21 wherein said acute angle is a divergence between said recess and said flexible member in a direction away from said second end.

23. The surgical scrub device according to claim 14 wherein said recess branches out into plural flow passages.

24. The surgical scrub device according to claim 14 wherein said flow passage means includes two tubes defined on opposite sides of said thin flexible member and projecting exteriorally from said second end of said handle.

25. The surgical scrub device according to claim 24 wherein each of said tubes includes a sharp-pointed termination disposed inside said handle member and projecting toward said first end, and wherein one of said tubes corresponds to said at least one spike.

26. The surgical scrub device according to claim 25 wherein said sharp pointed terminations are transversely spaced, each termination being disposed in respective intersecting biased planes.

27. A surgical scrub device comprising:
an elongated hollow handle member having first and second longitudinally-spaced ends, said first end being open;
an absorbent applicator member disposed about said second end of said handle member;
an elongated fluid-containing cartridge adapted for longitudinal slidability in said handle member, said cartridge having a rupturable forward end by which it is inserted into said open first end of said handle member; and
at least one hollow spike formed as part of and inside said handle member proximate said second end, said spike having a pointed end projecting longitudinally toward said first end and providing full flow communication from within said handle member to said applicator member through said second end of said handle member, said hollow spike being interiorally coated with a non-wetting material.

28. A surgical scrub device according to claim 27 wherein said non-wetting material is silicone.

* * * * *